US006980285B1

(12) United States Patent
Hansen

(10) Patent No.: US 6,980,285 B1
(45) Date of Patent: Dec. 27, 2005

(54) METHOD IN QUALITY CONTROL OF A SPECTROPHOTOMETER

(75) Inventor: Heine Hansen, Ølstykke (DK)

(73) Assignee: Radiometer Medical A/S, Brønshøj (DK)

(*) Notice: Subject to any disclaimer, the term of this patent is extended or adjusted under 35 U.S.C. 154(b) by 0 days.

(21) Appl. No.: 09/719,415

(22) PCT Filed: Jun. 10, 1999

(86) PCT No.: PCT/DK99/00313

§ 371 (c)(1),
(2), (4) Date: Apr. 4, 2001

(87) PCT Pub. No.: WO99/66310

PCT Pub. Date: Dec. 23, 1999

(30) Foreign Application Priority Data

Jun. 12, 1998 (DK) .................................. 1998 00783

(51) Int. Cl.[7] .................. G01N 33/48; G01N 21/00; G01J 3/42
(52) U.S. Cl. .................. 356/41; 356/319; 356/432
(58) Field of Search ................ 356/39–42, 319, 356/326, 300, 440–442, 432–436; 250/252.1; 702/85

(56) References Cited

U.S. PATENT DOCUMENTS

| | | | | |
|---|---|---|---|---|
| 3,638,640 A | * | 2/1972 | Shaw .................. 600/323 |
| 5,243,546 A | * | 9/1993 | Maggard .................. 702/90 |
| 5,397,899 A | * | 3/1995 | DiFoggio et al. ...... 250/339.09 |
| 5,459,677 A | * | 10/1995 | Kowalski et al. .............. 703/2 |
| 5,553,615 A | * | 9/1996 | Carim et al. ................ 600/324 |
| 5,568,400 A | * | 10/1996 | Stark et al. .................... 702/85 |
| 5,592,291 A |   | 1/1997 | Iida |
| 5,724,268 A | * | 3/1998 | Sodickson et al. ............ 702/33 |
| 5,828,445 A | * | 10/1998 | Scharlack .................... 356/40 |
| 5,933,792 A | * | 8/1999 | Andersen et al. ............. 702/32 |
| 6,029,115 A | * | 2/2000 | Tracy et al. .................. 702/22 |
| 6,064,899 A | * | 5/2000 | Fein et al. .................. 600/323 |
| 6,103,197 A | * | 8/2000 | Werner .................... 422/82.09 |
| 6,262,798 B1 | * | 7/2001 | Shepherd et al. ............. 356/39 |
| 2001/0020123 A1 | * | 9/2001 | Diab et al. .................. 600/323 |

FOREIGN PATENT DOCUMENTS

| | | | |
|---|---|---|---|
| EP |    132399 A1 | * 1/1985 | .......... G01N/33/52 |
| EP | 0 167 816 A2 | 1/1986 | |
| JP |    90-15048 | 1/1997 | |
| JP |    10-142054 | 5/1998 | |
| WO | WO 94/08225 | 4/1994 | |
| WO | WO 96/30742 | 10/1996 | |
| WO | WO 97/01751 | 1/1997 | |

OTHER PUBLICATIONS

Allen, Fritz et al.; Jun. 1998; U.S. Appl. No. 60/088,816.*

* cited by examiner

Primary Examiner—Zandra V. Smith
Assistant Examiner—Gordon J. Stock, Jr.
(74) Attorney, Agent, or Firm—Bryan Cave LLP

(57) ABSTRACT

The present invention relates to a method in quality control of a spectrophotometer, comprising the steps of determining with the spectrophotomer a spectrum $A_m(\lambda)$ of a fluid QC sample containing a dye, and determining a wavelength shift $\Delta\lambda$ from $C_{\Delta\lambda}(\lambda)$, $A_m(\lambda)$, in which $C_{\Delta\lambda}(\lambda)$ is a predetermined coefficient vector previously stored in a memory of the spectrophotometer.

37 Claims, 9 Drawing Sheets

| | Concentrations, mmol/kg water | | | |
|---|---|---|---|---|
| Component | QC level 1 | QC level 2 | QC level 3 | QC level 4 |
| PIPES, Na-salt | - | - | - | 64.2742 |
| HEPES | 40.7286 | 31.0138 | 24.2665 | - |
| HEPES, Na-salt | 20.0250 | 33.2875 | 39.6078 | - |
| NaCl | 115.1848 | 82.6968 | 44.7194 | 15.9993 |
| KCl | 2.0400 | 4.1068 | 6.1508 | 7.6600 |
| $NaHCO_3$ | 25.348 | 28.38 | 21.9319 | 19.6667 |
| $CaCl_2 2H_2O$ | 1.2502 | 0.5999 | 0.3455 | 2.2201 |
| TRISxHCl | 8.6434 | 14.217 | 7.7588 | - |
| TRIS | 1.7789 | 5.2435 | 24.9175 | - |
| Sulforhodamine B, Na-salt | 1.0023 | 1.6705 | 2.5058 | 0.3444 |
| Glucose | 2.5710 | 6.178 | 15.5218 | - |
| Lactate, Na-salt | 5.1427 | 1.5445 | 12.2997 | - |

FIG. 4

| Level | ctHb [g/dL] | sO$_2$ [%] | FO$_2$Hb [%] | FHHb [%] | FCOHb [%] | FMetHb [%] |
|---|---|---|---|---|---|---|
| 1 | 7.80 ±0.12 | 50.00 ±0.09 | 44.50 ±0.26 | 44.50 ±0.43 | 6.00 ±0.66 | 5.00 ±0.03 |
| 2 | 13.00 ±0.20 | 97.00 ±0.62 | 92.15 ±0.46 | 2.85 ±0.62 | 3.00 ±1.15 | 2.00 ±0.07 |
| 3 | 19.50 ±0.29 | 70.00 ±0.25 | 49.00 ±0.40 | 21.00 ±0.42 | 20.00 ±0.78 | 10.00 ±0.04 |
| 4 | 2.60 ±0.04 | 5.00 ±0.00 | 3.50 ±0.02 | 66.50 ±0.29 | 10.00 ±0.23 | 20.00 ±0.08 |

METHOD IN QUALITY CONTROL OF A SPECTROPHOTOMETER

FIELD OF THE INVENTION

The present invention relates to a method in quality control of a spectrophotometer for monitoring performance of the spectrophotometer, such as an oximeter for measurement of blood parameters.

BACKGROUND OF THE INVENTION

Spectrophotometers for measuring the composition of a substance by absorption spectroscopy are well known. For example, oximeters are used to determine concentrations of various hemoglobin components or fractions in blood samples from measuring an absorption spectrum in the visible and/or infrared wavelength range. Such an oximeter is disclosed in EP 210417.

In absorption spectroscopy, determination of a spectrum of a fluid sample is performed by transmission of light through a cuvette containing a part of the sample.

Absorption spectroscopy is based on Lambert-Beer's law according to which the absorbance determined for a sample containing a single optically active component (a dye) is directly proportional to the concentration of the component and the length of the light path through the sample in the cuvette:

$$A(\lambda) = \epsilon(\lambda) c d \quad (1)$$

in which $A(\lambda)$ is the determined absorbance at wavelength $\lambda$, $\epsilon(\lambda)$ is the molar extinction coefficient for the component at wavelength $\lambda$, c is the molar concentration of the component, and d is the length of the light path through the cuvette holding the sample.

The absorbance $A(\lambda)$ of the sample is defined as the logarithm of the ratio of the light intensity before and after transmission through the sample. In practice the absorbance $A(\lambda)$ is defined as the logarithm of the ratio between the light intensity, $I_0$, transmitted through a transparent aqueous reference solution and the light intensity transmitted through the sample:

$$A(\lambda) = \log \frac{I_0}{I} \quad (2)$$

For samples containing more than one optically active component, the total absorbance $A_{total}$ is the sum of the individual components' absorbances since absorbance is an additive quantity. Thus, while Y optically active components in a sample the total absorbance is given by $$A_{total}(\lambda) = \sum_{y=1}^{Y} \varepsilon_y(\lambda) c_y d \quad (3)$$

In a sample spectrum, the absorption $A_{total}(\lambda)$ recorded at each wavelength $\lambda$ contains contributions from each of the components in the same. The magnitude of this contribution and thereby the concentration of each component in the sample is determined according to $$c_y = \sum_{j=1}^{J} K_y(\lambda_j) A_{total}(\lambda_j) \quad (4)$$

in which

J is the total number of wavelengths $\lambda_j$ at which absorption is determined by the spectrophotometer and $K_y(\lambda_j)$ is a constant specific for component y at wavelength $\lambda_j$.

The vectors $K_y(\lambda)$ may be determined mathematically by using methods such as multivariate analysis, or solving n equations with n unknowns, on data from reference samples.

It is also known to monitor performance of spectrophotometers, such as oximeters, by a measuring the absorption spectrum of a fluid quality control sample, QC sample, with the spectrophotometer in question.

Known quality control samples specific for blood analysis are typically red dye based samples designed to simulate the spectrum of blood. In addition to a red dye, they sometimes contain certain amounts of oxygen, carbon dioxide, and electrolytes at an established pH for determining performance of blood gas and electrolyte instruments. Synthetic QC samples having an absorption spectrum that closely mimics that of physiological blood have not yet been provided.

Quality control of the spectrophotometers, such as an oximeter, is typically performed by measuring the absorption spectrum of a QC sample comprising three to four different dyes. The dyes are mixed in a proportion so that the QC sample absorption spectrum mimics the absorption spectrum of blood. A spectrum of a QC sample is measured on the oximeter to be monitored and the parameter values determined by the oximeter are compared with predetermined control limits assigned to the QC sample by a qualified person. If the determined parameters are outside the corresponding control limits, servicing of the oximeter is required.

In WO 96/30742 a quality control method for monitoring performance of an oximeter is disclosed. The method comprises measuring the absorption spectrum of a QC sample and comparing it to a standard spectrum of the QC sample. Instrumental errors of the oximeter are considered to be the primary source contributing to the observed difference. Instrumental errors are converted into blood component concentration values to that instrument errors can be reported in terms understood by the operator of the instrument.

It is an important disadvantage of known quality control methods that, typically, known QC samples comprise 3–4 different dyes, causing long-term stability of the sample to be less than desired. To compensate for this, parameter value acceptance ranges in an oximeter may be widened leading to a more relaxed performance monitoring than desired.

It is another important disadvantage of known quality control methods that it is impossible with known quality control methods to distinguish between different types of instrument errors and to determine an individual contribution to deviation in parameter values from a specific type of instrument error. Thus, parameter value acceptance ranges have to be sufficiently wide to accommodate any possible type of instrument error. Further, a quality controlled spectrophotometer cannot be diagnosed if the determined parameter values lie outside the acceptable ranges. For example, a defect spectrophotometer with a wavelength shift may introduce the same deviation in the determined parameters as seen by dilution of the QC sample.

Future spectrophotometers are expected to facilitate determination of absorption spectra with improved resolution whereby instruments of higher precision and specificity are provided. High resolution measurements of spectra makes it more difficult to develop a suitable QC sample since precision and long term stability requirements are increased.

One of the most significant errors occurring in spectrophotometers is a wavelength shift. Due to manufacturing tolerances and drift during use, each spectrophotometer positions a determined spectrum slightly differently along the wavelength axis. Therefore, the wavelengths at which absorbance is determined are also positioned slightly differently for different spectrophotometers and thus, determined absorbances will vary for different spectrophotometers.

SUMMARY OF THE INVENTION

It is an object of the present invention to provide a quality control method that facilitates the determination of various types of spectrophotometers errors, whereby an accurate diagnosis of an instrument failing the QC test is provided.

An instrument error affects the spectrum of a sample, and specific types of instrument errors affect the spectrum in a distinct way that may be interpreted like the presence of a component in the sample in a different concentration. For example, a variation of the length d of the light path through the cuvette causes determined absorbances $A(\lambda)$ to vary according to Lambert-Beer's law (absorbance is proportional to d), and unintentional dilution of the sample in the cuvette affects the determined absorbance in the same way, etc.

An absorption spectrum of a sample may be defined by a vector $A_m(\lambda)$ comprising at least two elements, each of the elements representing an absorbance of the sample at a specific wavelength $\lambda_j$.

According to a first aspect of the invention a quality control method for a spectrophotometer is provided, comprising the steps of:

determining with the spectrophotometer an absorption spectrum $A_m(\lambda)$ of a fluid quality control sample containing a dye selected from such dyes which provide the quality control sample with an absorption spectrum with a significant absorbance peak showing a steep flank, and determining a wavelength shift $\Delta\lambda$ between the absorption spectrum $A_m(\lambda)$ of the actually measured quality control sample and a reference absorption spectrum $A_0(\lambda)$ of a reference quality control sample containing the dye stored in a memory of the spectrophotometer.

According to a preferred embodiment of the invention a method is provided, wherein the wavelength shift $\Delta\lambda$ is determined from $A_m(\lambda)$ and a predetermined mathematical parameter stored in the memory of the spectrophotometer.

According to a further preferred embodiment of the invention a method in quality control of a spectrophotometer is provided, comprising the steps of determining with the spectrophotometer a spectrum $A_m(\lambda)$ of a fluid QC sample containing a dye, and determining a wavelength shift $\Delta\lambda$ from $C_{\Delta\lambda}(\lambda) \cdot A_m(\lambda)$, in which $C_{\Delta\lambda}(\lambda)$ is a predetermined coefficient vector previously stored in a memory of the spectrophotometer.

In a preferred embodiment of the invention a method is provided, wherein the vector $C_{\Delta\lambda}(\lambda)$ fulfils the equation $$\Delta\lambda = C_{\Delta\lambda}(\lambda) \cdot A_m(\lambda) \tag{5}$$

According to a preferred embodiment of the invention the wavelength shift of a spectrophotometer is determined by forming a Taylor series of a known absorption spectrum of a reference spectrum of a certain component in a sample. After determination of an absorption spectrum of a sample comprising the component with the known absorption spectrum, the wavelength shift is determined.

In a preferred embodiment of the method according to the invention the wavelength of shift $\Delta\lambda$ is determined after normalisation of the determined spectrum $A_m(\lambda)$ with an estimate of the concentration of the dye.

In a further preferred embodiment of the method according to the invention $C_{\Delta\lambda}(\lambda)$ has been determined from a combination of a reference spectrum $A_C(\lambda)$ of a reference sample containing the dye and a first derivative $A_0'(\lambda)$ of the reference spectrum.

In an approximation, only the first order derivative of the reference spectrum is considered:

$$A_m(\lambda) = A_0(\lambda) + \Delta\lambda A_0'(\lambda) \tag{6}$$

in which $A_0(\lambda)$ is the reference spectrum, $A_0'(\lambda)$ is its first derivative with respect to the wavelength $\lambda$, $\Delta\lambda$ is the wavelength shift to be determined, and $A_m(\lambda)$ is a spectrum of the sample with the known spectrum $A_0(\lambda)$ measured by the spectrophotometer in which the wavelength shift is to be determined.

$\Delta\lambda$ may be determined according to various mathematical methods known in the art, e.g. the equation above may be solved for a selected wavelength, the equation may be solved for a set of selected wavelengths and $\Delta\lambda$ be calculated as an average of the solutions for $\Delta\lambda$ to the equation, $\Delta\lambda$ may be determined by a least squares fit, $\Delta\lambda$ may be determined by multivariate analysis, etc.

In a preferred embodiment of the invention a method of preparing a spectrophotometer for quality control is provided, comprising the steps of determining a first reference spectrum $A_0(\lambda)$ of a reference sample containing a dye of a first concentration with a reference spectrophotometer, determining a first derivative $A_0'(\lambda)$ of the first reference spectrum of the dye, and determining from at least the first reference spectrum $A_0(\lambda)$ and the first derivative of $A_0(\lambda)$ a mathematical parameter from which a wavelength shift $\Delta\lambda$ of the spectrophotometer can be determined, and storing the mathematical parameter in a memory of the spectrophotometer.

Preferably, the step of determining a mathematical parameter comprises the steps of calculating a set of calibration vectors $B_i(\lambda)$ according to $$B_i(\lambda) = s_i A_0(\lambda) + s_{i3} A_0'(\lambda) \tag{7}$$

in which $i = 1, 2, \ldots, N$ ($N \geq 1$) and $s_i$ and $s_{i3}$ are constants of selected values, determining a coefficient vector $C_{\Delta\lambda}(\lambda)$ constituting the mathematical parameter so that each set of corresponding values $s_{i3}$, $B_i$ satisfies:

$$s_{i3} = c_{\Delta\lambda}(\lambda) \cdot B_i(\lambda), \ i = 1, 2, \ldots, N \tag{8}$$

According to a second aspect of the invention a spectrophotometer is provided comprising a processor that is adapted to determine the wavelength shift $\Delta\lambda$ between an absorption spectrum $A_m(\lambda)$ determined with the spectrophotometer on a fluid quality control sample containing a dye selected from such dyes which provide the quality control sample with an absorption spectrum with a significant absorbance peak showing a steep flank and a reference absorption spectrum $A_0(\lambda)$ of a reference quality control sample containing the dye, stored in the memory of the spectrophotometer.

According to a preferred embodiment of the invention a spectrophotometer is provided comprising a memory with a mathematical parameter for the determination of a wavelength shift $\Delta\lambda$ of the spectrophotometer, and a processor that is connected to the memory and that is adapted to calculate the wavelength shift $\Delta\lambda$ from the mathematical parameter and from a spectrum $A_m(\lambda)$ determined with the spectrophotometer on a fluid QC sample containing a dye.

According to a further preferred embodiment of the invention a spectrophotometer is provided, wherein the mathematical parameter is a coefficient vector $C_{\Delta\lambda}(\lambda)$ and wherein the wavelength shift $\Delta\lambda$ is determined from $C_{\Delta\lambda}(\lambda) \cdot A_m(\lambda)$.

In a preferred embodiment of the invention a spectrophotometer is provided, wherein the vector $C_{\Delta\lambda}(\lambda)$ fulfils the equation $$\Delta\lambda = C_{\Delta\lambda}(\lambda) \cdot A_m(\lambda) \tag{5}$$

The mathematical parameter as mentioned above may comprise the first reference spectrum $A_0(\lambda)$ and the first derivative $A_0'(\lambda)$ of the first reference spectrum $A_0(\lambda)$ at a selected wavelength $\lambda_0$ or at a selected set of wavelengths $\lambda_0, \lambda_1 \ldots, \lambda_L$, etc., or a parameter derived from the spectra, such as the parameter $C_{\Delta\lambda}(\lambda)$.

Since the parameter $\Delta\lambda$ is proportional to a total concentration $c_{qc}$ of the dye, $\Delta\lambda$ is typically normalised with $c_{qc}$ or an approximation to $c_{qc}$, e.g. when the dye is a two-component dye, such as Sulforhodamine B, $\Delta\lambda$ is preferably normalised with a concentration of a first component of the dye $s_1$. The normalisation of $\Delta\lambda$ with $s_1$ is desirable when there is a difference between the concentration of the dye in a reference sample from which the reference spectrum was determined, and the concentration of the dye in the QC sample.

Thus, in a preferred embodiment of the spectrophotometer according to the invention, the mathematical parameter stored in the memory constitutes a vector $C_{\Delta\lambda}(\lambda)$ from which the wavelength shift $\Delta\lambda$ may be determined.

According to a further preferred embodiment of the invention, the QC sample comprises a dye with two components in a chemical equilibrium where the ratio between the concentration of each component varies with the total concentration of the dye. In this case the shape of the absorption spectrum is dependent on the total concentration of the dye. This characteristic of the dye makes it possible to distinguish between a concentration measurement error caused by undesired dilution of the sample in the cuvette, and a measurement error caused by light path changes in the cuvette.

Thus, the method of preparing a spectrophotometer for quality control may comprise determining a first reference spectrum $A_{01}(\lambda)$ of a reference sample containing the dye in a first concentration and determining a second reference spectrum $A_{02}(\lambda)$ of a reference sample containing the dye in a second concentration with the reference spectrophotometer, the dye comprising a first component and a second component in chemical equilibrium. Mathematically two model spectra $A_1(\lambda)$ and $A_2(\lambda)$ that represent spectral information about the first and the second component, respectively, may be derived from the first and second reference spectra $A_{01}(\lambda)$ and $A_{02}(\lambda)$ in such a way that the spectra of the reference samples can be calculated as a weighted sum of $A_1(\lambda)$ and $A_2(\lambda)$. For example, $A_1(\lambda)$ and $A_2(\lambda)$ may be the individual spectra from the two components, respectively, of the dye, or, $A_1(\lambda)$ may be the sum of the individual spectra from the two components while $A_2(\lambda)$ may be the difference between the individual spectra of the two components, etc. Preferably, $A_1(\lambda)$ and $A_2(\lambda)$ are determined from reference spectra $A_{01}(\lambda)$ and $A_{02}(\lambda)$ by Principal Components Analysis (PCA).

The spectrum $A_m(\lambda)$ determined by the spectrophotometer is then given by $$A_m(\lambda) = s_1 A_1(\lambda) + s_2 A_2(\lambda) + \Delta\lambda A_0'(\lambda) \tag{9}$$

Each of the parameters $s_1$, $s_2$, and $\Delta\lambda$ may be determined by mathematical methods, such as multivariate analysis on data obtained from reference samples.

In a preferred embodiment of the invention, the step of determining a mathematical parameter may comprise the steps of calculating a set of vectors $B_i(\lambda)$ from $$B_i(\lambda) = s_{i1} A_1(\lambda) + s_{i2} A_2(\lambda) + s_{i3} A_0'(\lambda) \tag{10}$$

in which $i = 1, 2, \ldots, N$ ($N \geq 1$) and $s_{i1}$, $s_{i2}$ and $s_{i3}$ are constants of selected values, determining a vector $C_{\Delta\lambda}(\lambda)$ constituting the mathematical parameter so that $$s_{i3} = C_{\Delta\lambda}(\lambda) \cdot B_i(\lambda), \ i = 1, 2, \ldots, N \tag{11}$$

Further, the mathematical parameter may comprise a vector $C_1(\lambda)$ fulfilling that $$s_{i1} = C_1(\lambda) \cdot B_i(\lambda), \ i = 1, 2, \ldots, N \tag{12}$$

and still further, the mathematical parameter may also comprise a vector $C_2(\lambda)$ fulfilling that $$s_{i2} = C_2(\lambda) \cdot B_i(\lambda), \ i = 1, 2, \ldots, N \tag{13}$$

According to a preferred embodiment of the invention, the method in quality control of a spectrophotometer may utilise a QC sample containing the dye in a known concentration $c_{qc}$ and comprising the first and second components, and may further comprise the steps of calculating parameters $s_1$ and $s_2$ from $$s_1 = C_1(\lambda) \cdot A_m(\lambda) \tag{14}$$

$$s_2 = C_2(\lambda) \cdot A_m(\lambda) \tag{15}$$

in which $C_1(\lambda)$ and $C_2(\lambda)$ are the predetermined vectors previously stored in the memory of the spectrophotometer, and calculating an estimated concentration $c_{est}$ of the dye from $$c_{est} = a \ s_1 + b \ s_2 \tag{16}$$

in which $a$ and $b$ are predetermined constant previously stored in the memory of the spectrophotometer, and $s_1$ and $s_2$ represents concentrations of a first and a second component, respectively, of the dye.

Likewise, in a preferred embodiment of the invention the memory of the spectrophotometer may further comprise vectors $C_1(\lambda)$ and $C_2(\lambda)$ fulfilling the equations (14) and (15).

The memory may also comprise predetermined constants $a$ and $b$ and the processor may be further adapted to calculate the concentration $c_{est}$ of the dye according to equation (16)

$$c_{est} = a \ s_1 + b \ s_2 \tag{16}$$

It is preferred that the dye has a spectrum with a significant absorbance peak with a steep flank within the measurement range of the spectrophotometer in order to accurately determine small wavelength shifts. For example, when the sample to be analysed is blood, a wavelength shift of 0.05 nm is sufficient to cause an inaccurate determination of several blood parameters, such as ctHb, $sO_2$, $FO_2Hb$, FHHb, FCOHb, FMetHb, etc.

Further, it is preferred that the spectrum of the QC sample resembles spectra of samples, which the spectrophotometer in question is intended to analyse so that performance of the instrument can be monitored.

For example, in blood analysis important blood components have significant absorbances in the wavelength range from 480 to 670 nm. Thus, a dye with a spectrum resembling a blood spectrum and having a significant absorbance peak in the range from 400 to 800 nm, preferably from 480 to 670 nm, and having a steep absorbance flank, such as a flank having steepness larger than 40 mAbs/nm, preferably larger than 50 mAbs/nm for a light path length of 100 $\mu$m, is preferred for use in the methods according to the present invention. The dye should, preferably, also have a molar extinction coefficient in the range from 10,000 to 100,000.

The dye may belong to one of several chemical classes, such as cyanine dyes, azacyanine dyes, triarylmethine dyes, acridine dyes, zine dyes, oxazine dyes, thiazine dyes, xanthene dyes, etc. Dyes belonging to the first four classes are typically cationic dyes being water soluble due to the molecule's positive charge. The xanthene dyes include the cationic and neutral rhodamines and the anionic sulforhodamines among which Sulforhodamine B is a preferred dye.

According to a preferred embodiment of the invention, the spectrum of reference samples containing the dye in at least two different concentrations is determined, e.g. by an accurate reference instrument of the same type as the spectrophotometer to be quality controlled, at a selected set of wavelengths. Then the coefficient vectors $C_1(\lambda)$, $C_2(\lambda)$ and $C_{A\lambda}(\lambda)$ and the constants a and b are determined, e.g. by multivariate analysis, and stored at the time of manufacture in the memory of the spectrophotometers to be quality controlled by fluid QC samples when put into their normal use.

On manufacture of a QC sample the concentration $c_{qc}$, the ratio $s_2/s_1$ denoted $Q_{qc}$ and an initial wavelength shaft $\Delta\lambda_{qc}$ may be determined by a reference spectrophotometer. The initial wavelength shift of the QC sample emerges mainly from a variation in the composition of the solvent of the dye in the QC sample.

A label, such as a bar-code label, a magnetic label, etc, may be attached to each of the QC samples containing one or more of the values $c_{qc}$, $Q_{qc}$ and $\Delta\lambda_{qc}$ in question. Alternatively one or more of the values may be printed in a bar code on a paper sheet following a set of QC samples. The values appearing on the labels or paper sheet are designated assigned values.

During quality control of a specific spectrophotometer, the assigned values of $c_{qc}$, $Q_{qc}$ and $\Delta\lambda_{qc}$ are read by the spectrophotometer and the values are stored in its memory. Then the spectrum of the QC sample is determine and $s_1$, $s_2$ and $\Delta\lambda$ are determined as previously described. The determined values for $Q_{est}=s_2/s_1$, $\Delta\lambda$ and $c_{est}$ are also calculated and compared to the assigned values of $Q_{qc}$, $\Delta\lambda_{qc}$ and $c_{qc}$, respectively.

A possible dilution of the QC sample may be determined from a difference between $Q_{est}$ and $Q_{qc}$, and the combined effect of dilution and deviations in length d of the light path through the cuvette may be determined from a difference between $c_{est}$ and $c_{qc}$.

The estimated parameters values, such as $\Delta\lambda$, $c_{est}$, and $Q_{est}$, may be used for determination of parameter values of samples, the analysis of which the spectrophotometer is intended for, so that the outcome of the quality control procedure can be reported by the instrument in quantities meaningful for an operator of the instrument.

For example, in an oximeter for determination of blood parameter values, the theoretical modifications to one or several predetermined standard blood spectra caused by a measurement error corresponding to one of the parameters $\Delta\lambda$, $c_{est}$, and $Q_{est}$ determined in the quality control procedure may be calculated by the oximeter. From the modified spectra, the oximeter may calculate corresponding blood parameter values to be reported to the operator of the instrument.

The predetermined standard blood spectra may either be stored in the memory of the oximeter, or they may be derived mathematically by the processor in the oximeter from predetermined spectra of each blood component comprised in the standard blood samples.

In a preferred embodiment of the invention predetermined control limits for the reported blood parameter values are printed on a sheet of paper following a set of QC samples. The operator may compare blood parameter values reported by the oximeter with the predetermined control limits on the paper sheet, and determine whether the reported values are within the control limits.

The predetermined control limits may also be stored in a label of the QC sample which label is read by the oximeter so that the oximeter is adapted to perform the comparison between the reported blood parameter values and the corresponding control limits.

In a preferred embodiment of the invention, a method for repressing absorption spectra of interfering components or substances in a fluid sample, is also provided.

In the present context an interfering component in a sample is a component other than the preselected components for which the spectrophotometer is adapted to report parameter values, and the presence of said interfering component in the sample may interfere with the absorption spectrum of at least one of said preselected components.

In a determined sample spectrum, the absorbance $A_m(\lambda)$ recorded at each wavelength $\lambda$ contains contributions from each of the components in the sample including said interfering components. The magnitude of the contribution and thereby the concentration of each component in the same is determined according to equation (17) or equation (18) below $$c_y = \sum_{j=1}^{J} K_y(\lambda_j) A_m(\lambda_j) \tag{17}$$

or the equivalent from $$c_y = K_y(\lambda) \cdot A_m(\lambda) \tag{18}$$

The vectors $K_y(\lambda)$ may be determined mathematically by using methods, such as multivariate data analysis, or solving n equations with n unknowns from data obtained from reference samples. By including one or several interfering components or substances in the reference sample, of which the reference spectrum is determined, one or several of the vectors $K_y(\lambda)$ corresponding to one or several of the interfering components may be determined. The vector or vectors $K_y(\lambda)$ corresponding to the interfering components are generally designated $K_{int}(\lambda)$ and stored in the memory of the spectrophotometer together with the vectors $K_y(\lambda)$.

The spectrophotometer may further provide one or several predetermined vectors, $A_{int}(\lambda)$, representing spectral information of the interfering components. Each $A_{int}(\lambda)$ is obtained at a reference concentration $c_{ref}$, whereby the spectrum of any interfering component may be derived at the determined concentration of the component according to Lambert-Beer's law, equation (1).

In this preferred embodiment of the invention, the effect of the interfering components on determined blood parameter values is minimised by following a three stage process, in the following denoted "repression of spectra of interfering components".

First stage is to determine the concentration of interfering components in the sample. Second stage is to determine a modified spectrum of the sample by subtracting the spectrum of the interfering component of the determined concentration from the measured spectrum $A_m(\lambda)$ of the sample. Third stage is to determine concentrations of blood components $c_y$ and parameter values of blood components from the modified spectrum.

According to this preferred embodiment of the invention, a spectrophotometer with repression of spectra of interfering components in a fluid sample is provided, for determination of a concentration $c_y$ of a component y of a sample and wherein the memory further comprises at least one vector $A_{int}(\lambda)$ representing spectral information of an interfering component in the sample at a concentration $c_{ref}$, and at least one vector $K_{int}(\lambda)$, and wherein the processor is further adapted to calculate the concentration $c_{int}$ of the interfering component according to $$c_{int}=K_{int}(\lambda) \cdot A_m(\lambda) \tag{19}$$

and if $c_{int}$ is greater than a predetermined threshold value, $c_{ref}$, modify the measured spectrum $A_{mod}(\lambda)$ according to $$A_{mod}(\lambda) = A_m(\lambda) - \frac{c_{int}}{c_{ref}} A_{int}(\lambda) \tag{20}$$

$A_{mod}(\lambda)$ being the modified spectrum, and determine $c_y$ from the modified spectrum $A_{mod}(\lambda)$ according to $$c_y=K_y(\lambda) \cdot A_{mod}(\lambda) \tag{21}$$

whereby the effect of interfering components on determined concentrations $c_y$ is minimised.

The measured spectrum is only modified if the determined concentration of the interfering component is above a predetermined threshold value. This is because the modification of the measured spectrum creates some undesired "process noise" in the modified spectrum, due to an uncertainty in the estimate of the spectrum of the interfering component. This addition of "process noise" in the modified spectrum is only justified when the concentration of the interfering component in the sample is larger than the threshold value.

An oximeter for blood analysis may provide several predetermined vectors for interfering components or substances of clinical importance and provide corresponding values of the vectors $K_{int}(\lambda)$ in the memory. The interfering components may be chosen among components, which have previously caused significant interference in oximetry measurements, such as Fetal Hemoglobin, Bilirubin, Cardio Green, Evans Blue, Methylene Blue, Intralipid, HiCN, SHb, etc. By repressing the spectra of these components an oximeter with better precision in measurement of blood parameter values than currently available instruments is provided.

BRIEF DESCRIPTION OF THE DRAWINGS

The invention will now be described with reference to the drawings, wherein

FIG. 4 shows compositions of QC samples levels 1–4, FIG. 7 is a table comprising parameter values of blood samples each related to one of QC sample levels 1–4.

DETAILED DESCRIPTION OF A PREFERRED EMBODIMENT

Figure 1:
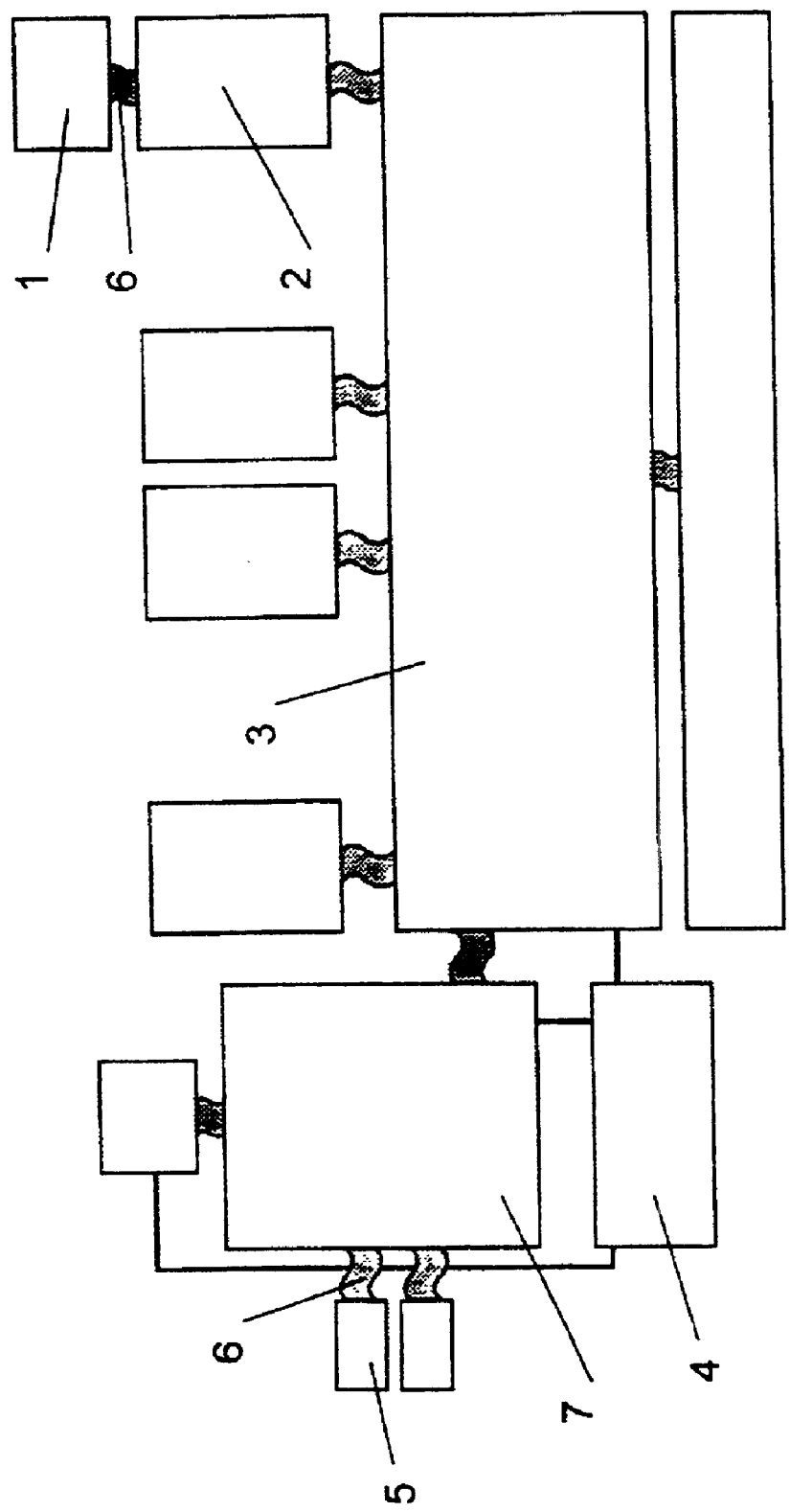
FIG. 1 is a block diagram of an oximeter according to the invention.

FIG. 1 is a block diagram comprising a spectrometer 1 in an oximetry module (not shown) connected to a printed circuit board 2 with a data cable 6 comprising electrical conductors. The printed circuit board 2 controls and collects data from the spectrometer 1. The data collected are transmitted to a data processing unit 3 comprising a memory (not shown) and a processor (not shown). Values of predetermined coefficient vectors $C_1(\lambda)$, $C_2(\lambda)$ and $C_{A\lambda}(\lambda)$ are stored in the memory. A barcode reader 5 is adapted to read data from bar-code labels mounted on QC samples or on a paper sheet enclosed with a set of samples, and transmits data to the data processing unit 3 via a data management computer 7. A power supply module 4 supplies power to the oximetry module from a mains connection.

Figure 2:
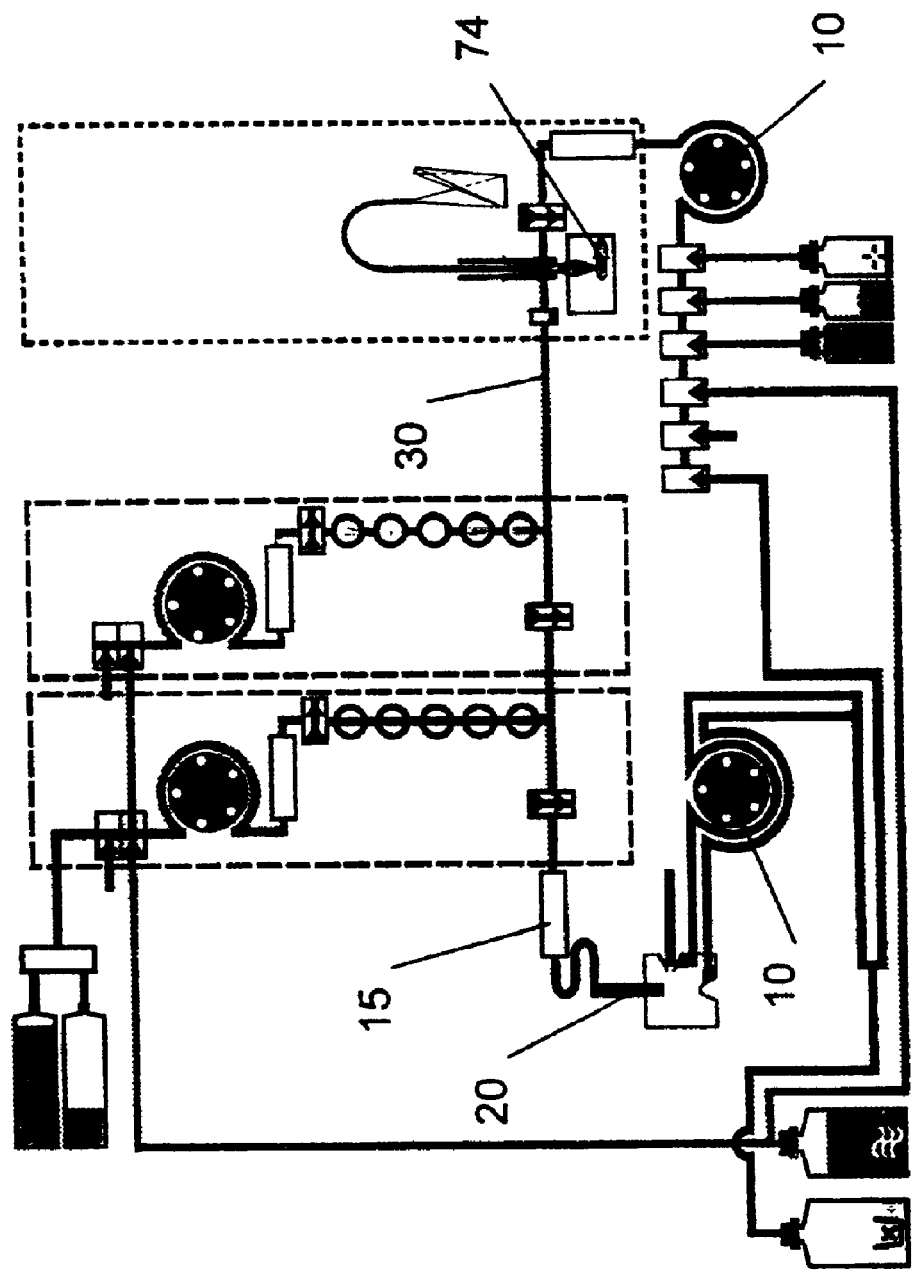
FIG. 2 is a schematic diagram of a wet section of an oximeter according to the invention.

FIG. 2 is a schematic diagram of a wet section of an oximeter according to the invention, wherein a blood sample (not shown) is entered into the oximeter through an inlet probe 20. The sample is transferred to a cuvette 74. A preheater 15 is positioned along the sample path 30 to heat the sample to a substantially constant temperature of 37° C. Pumps 10 are used to pump liquids and gasses through the wet section.

Figure 3:
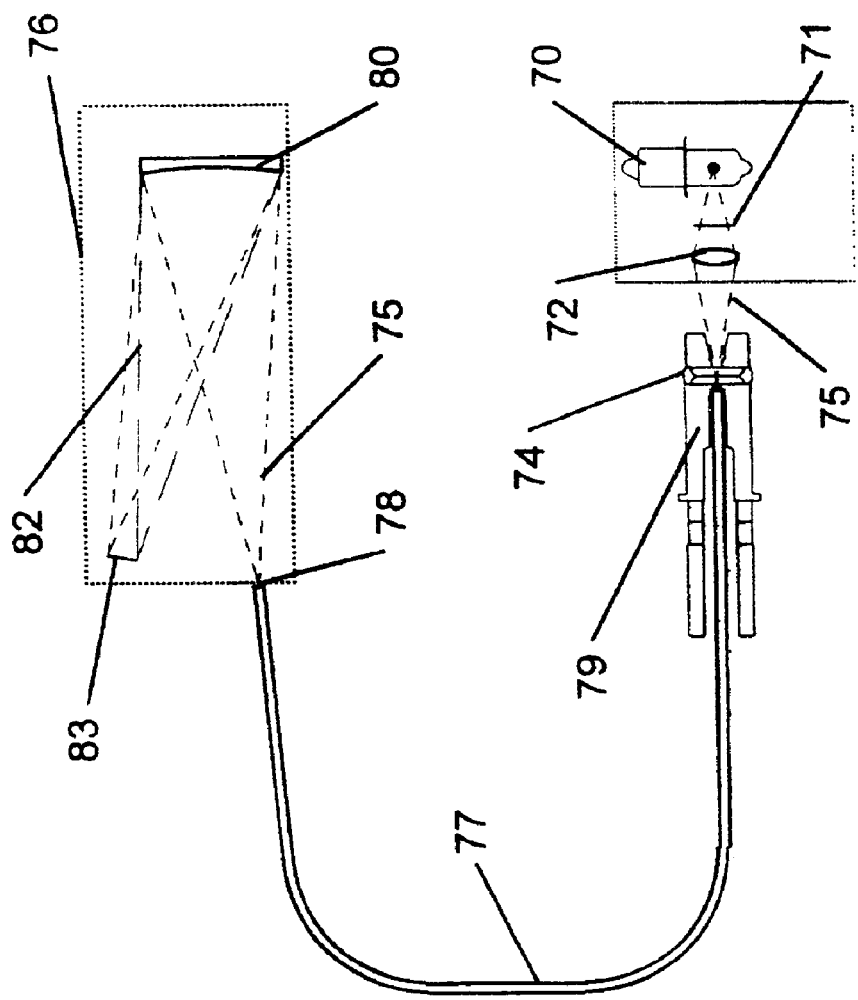
FIG. 3 shows main components of a spectrometer, i.e. the optical part of an oximeter according to the invention.

FIG. 3 shows the main components of the spectrometer 1, wherein a light beam 75 with constant intensity is transmitted from a halogen lamp 70 to the cuvette 74 which comprises the blood or QC sample and is included in a hemolyzer 79. The blood sample is hemolyzed by means of ultrasonic waves. Hemolyzing is a process, which ruptures the walls of the red blood cells in the sample, thereby making the blood cells release their content of hemoglobin.

The light beam 75 is transmitted to the cuvette 74 through an infrared filter 71, and a biconvex lens 72. After passing through the cuvette 74, the light beam 75 is transmitted to a measurement section 76, by means of an optical fiber 77. The light beam 75 passes through thin slit 78, whereby the beam 75 is directed towards a concave grating unit 80, diffracting the light beam 75 according to wavelength.

The concave grating unit 80 focuses light on a photodiode array 83, to which a diffracted light beam 82 is transmitted. The photodiode array 83 may consist of 128 photodiodes, and the array 83 is arranged in such a manner that light comprising a range of wavelengths of approximately 1.5 nm in the diffracted light beam 82, strike a photodiode (not shown), which converts the light into a current substantially proportional to the light intensity which strikes it. By measuring the value of the current in each of the 128 photodiodes of the photodiode array 83, a discrete intensity spectrum of the light beam 82 after transmission through the sample is produced. From this intensity spectrum an absorption spectrum of the blood sample comprised in the cuvette 74 may be determined by the oximeter.

The absorption spectrum is measured in 128 channels located in the wavelength range 478–672 nm in the preferred embodiment of the invention. A channel is, in the present context, the part of the spectrum which is transmitted to a particular photodiode in the diode array 83.

According to the invention a wavelength shift of the oximeter is determined in the quality control procedure. It is preferred that four different types of quality control samples (QC samples levels 1–4) are provided, cf. FIG. 4. The QC levels comprise Sulforhodamine B in different concentrations. Increased reliability in the quality control of the oximeter is provided by measuring the absorption spectrum of QC samples at several QC levels. By utilising QC samples comprising Sulforhodamine B in different concentrations, it is ensured that the oximeter measures blood parameters correctly over a wide range of component concentrations in blood samples.

In solution Sulforhodamine B shows long term stability. The steep absorbance flank allows an accurate determination of the wavelength shift of the oximeter, since even very small wavelength shifts produce a large change in the measured absorbance at a given wavelength of a Sulforhodamine B containing sample.

In aqueous solution Sulforhodamine B is a dye with two components in a chemical equilibrium where the ratio between the concentration of each component in the dye varies with the total concentration of the dye. In this case the shape of the absorption spectrum is dependent on the total concentration $c_i$ of the dye. This may be seen in FIG. 5, which shows three absorption spectra $A_{01}(\lambda)$ 110, $A_{02}(\lambda)$ 111 and $A_{03}(\lambda)$ 112 of Sulforhodamine B samples determined at the total concentrations 2.5058 mmol/kg, 1.6705 mmol/kg and 1.0023 mmol/kg, respectively. The Sulforhodamine B samples correspond to QC levels 1–3 as shown in FIG. 4.

Figure 5:
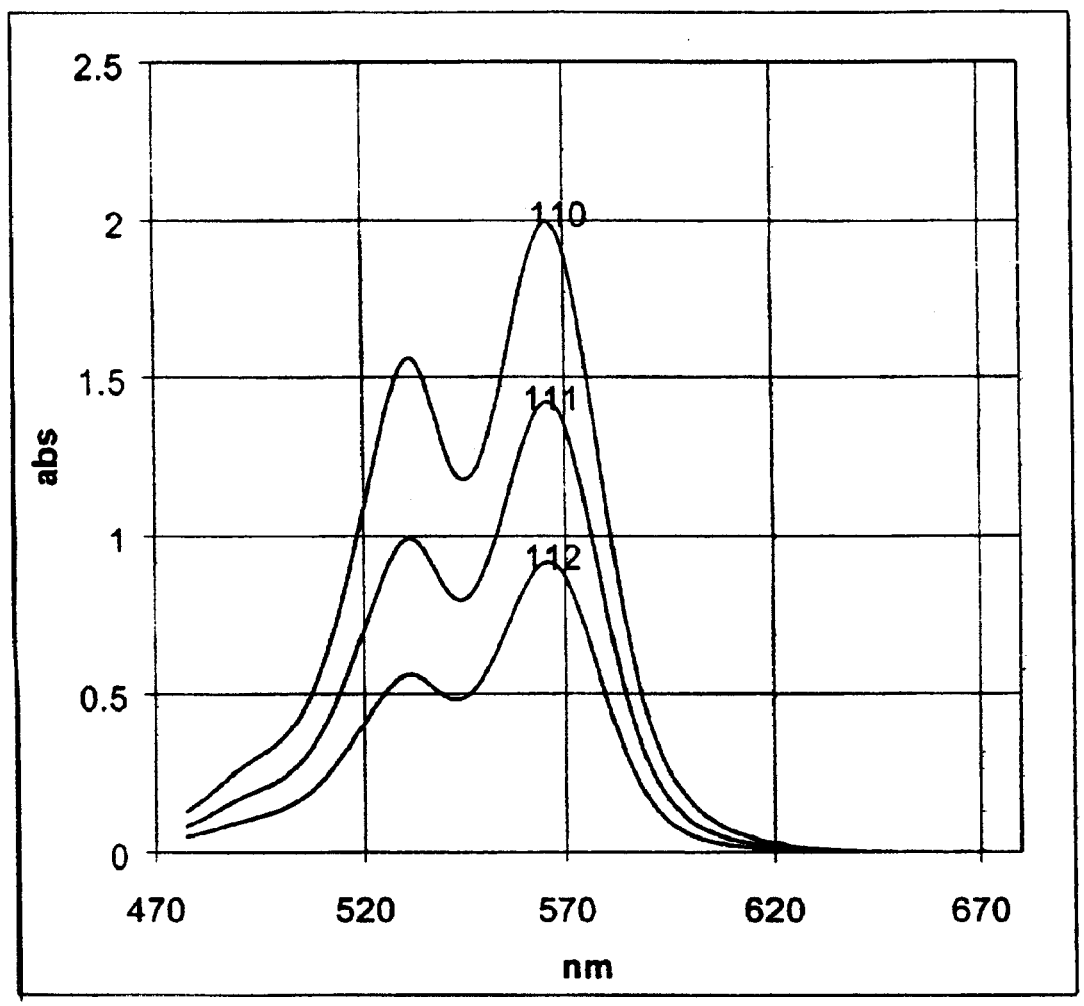
FIG. 5 shows absorption spectra of Sulforhodamine B in three concentrations.
Figure 6:
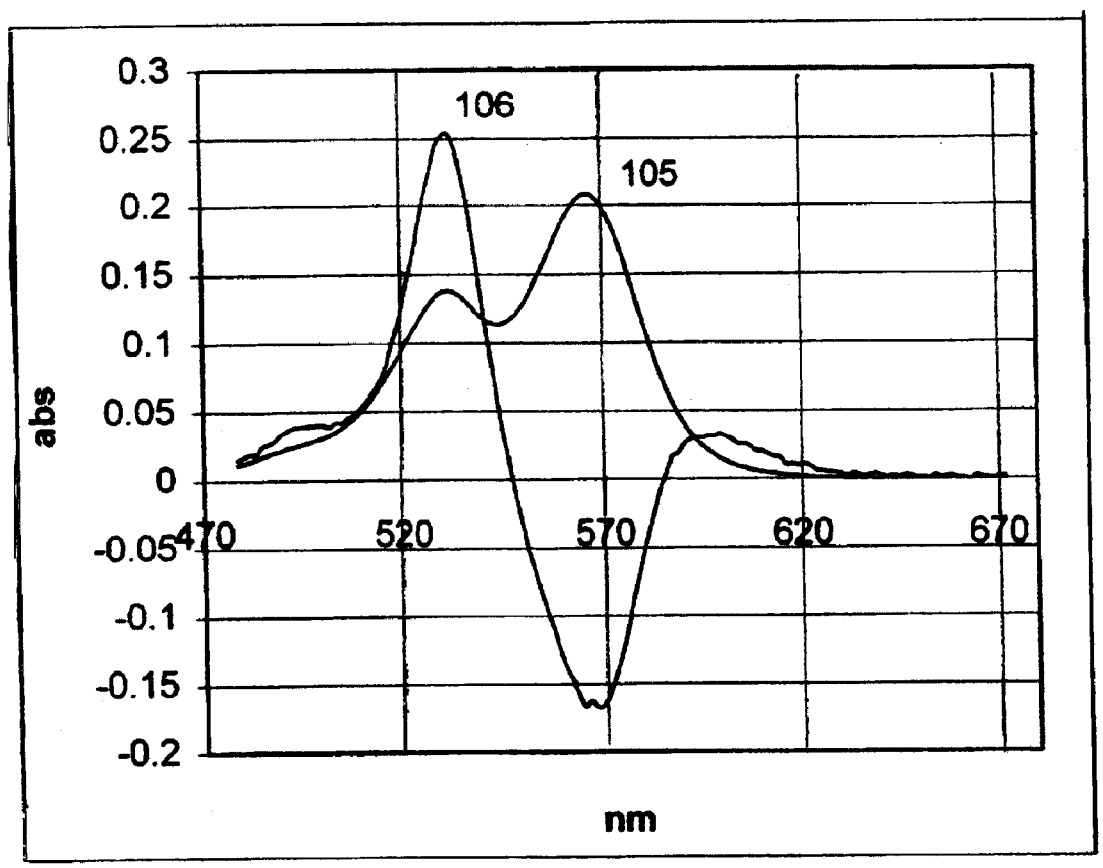
FIG. 6 shows two normalised model spectra determined with Principal Component Analysis from Sulforhodamine B.

Mathematically, two model spectra $A_1(\lambda)$ 105 and $A_2(\lambda)$ 106 as shown in FIG. 6 may be derived from at least two reference spectra, e.g. $A_{01}(\lambda)$ 110 and $A_{02}(\lambda)$ 111 of FIG. 5, wherein the two model spectra represent spectral information about a first and a second component, respectively of Sulforhodamine B, in such a way that the spectrum of the dye can be calculated as a weighted sum of $A_1(\lambda)$ and $A_2(\lambda)$.

The two model spectra are, preferably, determined by Principal Component Analysis (PCA), whereby two orthogonal vectors are determined constituting the mathematical model spectra, $A_1(\lambda)$ and $A_2(\lambda)$. A set of scores of parameters $s_{i1}$ and $s_{i2}$ is also provided by the PCA analysis for each concentration of the dye, as the spectrum of the dye at a concentration $c_i$ can be calculated as a weighted sum of model spectra $A_1(\lambda)$ and $A_2(\lambda)$ and their corresponding scores or weights $s_{i1}$ and $s_{i2}$.

The PCA analysis may be provided by several computer programs, which are commercially available. The program used in the present embodiment is the "Unscrambler". The two model spectra $A_1(\lambda)$ 105 and $A_2(\lambda)$ 106 shown in FIG. 6 are determined by PCA from the three reference spectra $A_{01}(\lambda)$, $A_{02}(\lambda)$ and $A_{03}(\lambda)$ with "Unscrambler".

The reference concentrations of the dye in the solution at which the reference absorption spectra $A_{01}(\lambda)$, $A_{02}(\lambda)$ and $A_{03}(\lambda)$ are measured, are determined from the weight of the dye, Sulforhodamine B in powder form and the volume of the solvent. The reference absorption spectra are determined by measuring the absorption spectra of 5 samples containing Sulforhodamine B at each reference concentration, and determining an average value for the reference spectrum for each concentration. The reference absorption spectra of the samples are measured by a reference oximeter, which by definition has a zero wavelength shift.

In practice, an oximeter not specifically appointed and handled as reference oximeter will always exhibit some wavelength shift $\Delta\lambda$ whereby a measured absorption spectrum $A_m(\lambda)$ of a sample will differ slightly from the reference spectrum $A_0(\lambda)$ of the same sample measured on the reference oximeter. The relationship between the measured spectrum $A_m(\lambda)$ and a reference spectrum $A_0(\lambda)$ and the model spectra is for small wavelength shifts according to equation (9).

$$A_m(\lambda) = s_1 A_1(\lambda) + s_2 A_2(\lambda) + \Delta\lambda A_0'(\lambda)$$

wherein $\Delta\lambda\, A_0'(\lambda)$ is the first term in a Taylor series of the reference spectrum $A_0(\lambda)$.

The first derivative of the reference spectrum $A_0'(\lambda)$ is preferably calculated in approximation as a first derivative of the model spectrum $A_1'(\lambda)$. The approximation is justified since the values of the scores $s_{i1}$ for the model spectra $A_1(\lambda)$ are found to be much higher than the values of the scores $s_{i2}$ for the model spectra $A_2(\lambda)$, of Sulforhodamine B in relevant concentrations $c_i$, so that $$A_0'(\lambda) = s_1 A_2'(\lambda) + s_2 A_2'(\lambda) = s_1 A_2'(\lambda) \quad (22)$$

whereby the measured spectrum $A_{mi}(\lambda)$ may be approximated by $$A_{m1}(\lambda) = s_{i1} A_1(\lambda) + s_{i2} A_2(\lambda) + \Delta\lambda_i s_{i1} A_1'(\lambda) \quad (23)$$

$\Delta\lambda_i s_{i1}$, $s_{i1}$, $s_{i2}$ are the scores or the constants corresponding to a concentration $c_i$.

Coefficient vectors $C_1(\lambda)$, $C_2(\lambda)$ and $C_{\Delta\lambda}(\lambda)$ are, preferably, determined by multivariate analysis from the scores and the corresponding determined absorption spectra.

The multivariate analysis starts by generating a table with 64 rows and 4 columns. The first three columns in this table comprise selected values of either one of the scores $\Delta\lambda_i s_{i1}$, $s_{i1}$, $s_{i2}$, and the last column comprises the corresponding calculated value of the spectrum $A_{mi}(\lambda)$. Each row constitutes a calibration vectors, and the entire table constitutes 64 calibration vectors.

The 64 values of each score appearing in one and the same column are evenly distributed between:

$$0 \text{ and } \frac{1}{\sqrt{A^2(\lambda_j)}}$$

wherein $A^2(\lambda_j)$ denotes the summation of squared absorbances across 128 wavelengths of the particular spectrum that corresponds to a particular score) i.e. the values of the score $s_{i1}$ are evenly distributed between 0 and reciprocal of (square root $(A_1^2(\lambda))$).

The next step in the multivariate analysis comprises to determine from the table the coefficient vector $C_1(\lambda)$ by Principal Component Regression so that each set of scores $s_{i1}$, and the corresponding spectrum $A_{mi}(\lambda)$, satisfies $$s_{i1} = C_1(\lambda) \cdot A_{mi}(\lambda) \qquad (24)$$

From the table the coefficient vector $c_2(\lambda)$ is determined by Principal Component Regression so that each set of scores $s_{i2}$ and the corresponding spectrum $A_{mi}(\lambda)$, satisfies $$s_{i2} = C_2(\lambda) \cdot A_{mi}(\lambda) \qquad (25)$$

From the table the coefficient vector $c_{\Delta\lambda}(\lambda)$ is determined by Principal Component Regression (PCR) so that each set of scores $\Delta\lambda_i s_{i1}$ and the corresponding spectra $A_{mi}(\lambda)$, satisfies $$\Delta\lambda_i \, s_{i1} = c_{\Delta\lambda}(\lambda) \cdot A_{mi}(\lambda) \qquad (26)$$

Further, it is assumed that the following relation between the calculated scores and a total concentration, $c_i$ of the dye exists.

$$c_i = a \, s_{i1} + b \, s_{i2} \qquad (27)$$

wherein constants a and b may be found by several methods, preferably, by inserting the determined scores from the total concentrations, $c_i$ of the dye concentrations 2.5058 mmol/kg and 1.0023 mmol/kg in equation (27) and solve the resulting two equations with two unknown quantities, for a and b. The determined values of a, b are: a=0.1425; b=0.0931, so that equation (27) is determined as $$c_i = 0.1425 \, s_{i1} + 0.0931 \, s_{i2} \qquad (28)$$

The validity of equation (28) may be checked by inserting scores $s_{i1}$, $s_{i2}$ from reference solutions with total concentrations $c_i$ of Sulforhodamine B not used in the determination of a and b. Thereby, the validity of equation (28) has been confirmed experimentally.

In field use of the spectrophotometer the coefficient vectors are applied as follows:

From the coefficient vector, $c_1(\lambda)$ a score or parameter value, $s_1$ may be determined according to equation (14)

$$s_1 = c_1(\lambda) \cdot A_m(\lambda)$$

wherein $A_m(\lambda)$ is a measured spectrum of a QC/reference sample.

From the coefficient vector, $c_2(\lambda)$ a score or parameter value, $s_2$ may be determined according to equation (15)

$$s_2 = c_2(\lambda) \cdot A_m(\lambda)$$

wherein $A_m(\lambda)$ is a measured spectrum of a QC/reference sample.

From the coefficient vector $c_{\Delta\lambda}(\lambda)$ a score or parameter value $\Delta\lambda s_1$, which is proportional to the wavelength shift may be determined according to $$\Delta\lambda s_1 = c_{\Delta\lambda}(\lambda) \cdot A_m(\lambda) \qquad (29)$$

wherein $A_m(\lambda)$ is a QC/reference sample.

Determined $s_1$, $s_2$ scores may be interpreted as the equivalent concentrations of the first and the second component of the dye, respectively. The first component corresponds to the mathematical model spectrum $A_1(\lambda)$, and the second component corresponds to the mathematical model spectrum $A_2(\lambda)$.

The determined coefficient vectors $C_{\Delta\lambda}(\lambda)$, $c_1(\lambda)$ and $c_2(\lambda)$ are stored in a matrix in the memory of the oximeter at the times of manufacture. The determined constants a, b are also stored in the memory of the oximeter at the time of manufacture.

QC samples are, preferably, manufactured in lots, which may comprise 40,000–50,000 samples. The lot values of $C_{qc}$, $Q_{qc}[[\text{ref}]]$ and $\Delta\lambda_{qc}$ are, preferably, determined during manufacturing by measuring 5–10 samples on 3 reference oximeters. The oximeters have been adjusted to report exact parameter values on a standard blood sample.

Average values of each of the measured parameters $c_{qc}$, $Q_{qc}[[\text{ref}]]$ and $\Delta\lambda_{qc}$ are calculated and preferably stored on a bar-code label attached to each of the QC samples.

During a quality control procedure of an oximeter in normal operation, e.g. at a hospital, the values of $c_{qc}$, $Q_{qc}[[\text{ref}]]$ and $\Delta\lambda_{qc}$ are read from the bar-code label of the QC sample by a bar-code reader and stored in the memory of the oximeter.

Then the absorption spectrum of the QC sample is determined. An estimated concentration of Sulforhodamine B in the QC sample may be determined by the measured absorption spectrum $A_m(\lambda)$ by equation (27) as $$c_{est} = 0.1425 \, s_1 + 0.0931 \, s_2$$

since the values of $s_1$ and $s_2$ can be determined by the measured absorption spectrum $A_m(\lambda)$ and the vectors $c_1(\lambda)$ and $c_2(\lambda)$ according to equations (14) and (15). The ratio between $s_1$ and $s_2$ is determined and denoted $Q_{est}$.

An estimate of a score proportional to the wavelength shift of the oximeter is provided by equation (26)

$$\Delta\lambda s_1 = c_{\Delta\lambda}(\lambda) \cdot A_m(\lambda)$$

Since the value of $s_1$ has been determined, the value of the wavelength shift of the oximeter is determined by dividing the score $\Delta\lambda s_1$ with $s_1$ $$\Delta\lambda = \frac{C_{\Delta\lambda}(\lambda) * A_m(\lambda)}{s_1} \qquad (30)$$

The length of the cuvette light path $d_0$ in the oximeter is, preferably, determined by measuring an absorption spectrum $A_m(\lambda)$ of a Sulforhodamine B reference solution. The concentration of Sulforhodamine B, $c_{ref}$, is, preferably, provided as an assigned value.

To determine the value of $d_0$, the absorption spectrum $A_m(\lambda)$ of the reference solution is measured, and an estimate of the concentration $c_{est}$ of the dye is calculated by the processor in the oximeter according to equations (27), (14), (15) by utilising predetermined coefficient vectors $c_{\Delta\lambda}(\lambda)$, $c_1(\lambda)$ and $c_2(\lambda)$ and constants a, b stored in the memory of the oximeter as previously described.

The concentration $c_{est}$ of the reference solution determined by the oximeter is utilised to calculate an actual value of the cuvette light path length, $d_0$, in the oximeter according to $$d_0 = d_{ref} \frac{c_{est}}{c_{ref}} \qquad (31)$$

wherein $d_{ref}$ is a reference value of the cuvette light path length, which is previously stored in the memory of the oximeter. The calculated value of $d_0$ is subsequently stored in the memory of the oximeter.

The difference between the value of $\Delta\lambda$ determined for the Sulforhodamine B reference solution and the assigned value $\Delta\lambda_{ret}$ for the reference solution is utilised to shift the subsequently measured spectra along the wavelength axis.

The absorbance $A(\lambda)$ of a fluid sample is measured by the oximeter by determining the logarithm of a light intensity $I_0$ transmitted through a transparent aqueous reference solution divided by the light intensity I transmitted through the fluid sample in question, according to equation (2)

$$A(\lambda) = \log\frac{I_0}{I}.$$

$I_0$ is denoted the zero point intensity, and is measured automatically at every calibration of the oximeter with said reference solution.

During a quality control of the oximeter, a determined value of $c_{est}$ may be compared with the corresponding value $c_{qc}$ read from the label of the QC sample. A difference between the values may originate from two of the variables in Lambert-Beer's law, equation (1)

$$A(\lambda) = \epsilon(\lambda) \, c \, d.$$

It applies that either the cuvette light path length d in the oximeter is different from the $d_0$ value stored in the memory of the oximeter, which causes a higher or a lower value of the measured absorbance, or the measured concentration $c_{est}$ of the dye deviates from the value of $c_{qc}$.

The determined concentration $c_{est}$ may deviate from the value of $c_{qc}$ due to errors in the wet section of the oximeter, such as defect tubes, defect pumps, errors in the cuvette, etc. It may all lead to undesired dilution of the sample. However $c_{est}$ may also be different from $c_{qc}$ due to an incorrect light path length $d_0$ of the cuvette.

If there is a difference between $c_{est}$ and $c_{qc}$, and the value of $Q_{qc}$[[ref]] being equal to $Q_{est}$, the difference between the estimated concentration and the reference concentration values may be caused by a difference between the light path length $d_0$ of the cuvette as calculated during calibration and the reference value $d_{ref}$ of the length determined during manufacture.

If there is a difference between $c_{est}$ and $c_{qc}$, the value of $Q_{qc}$[[ref]] being different from $Q_{est}$, the sample may be diluted. A dilution causes the concentration of the dye to be smaller than $C_{ref}$ and further causes a shift in the chemical equilibrium between the components $s_1$ and $s_2$ which causes the value of $Q_{est}$ to deviate from $Q_{qc}$[[ref]].

The determined differences between measured parameters $\Delta\lambda$, $c_{est}$, and $Q_{est}$ and the corresponding parameters read from the bar-code label of the QC sample may be reported by the oximeter to the operator e.g. by means of a printer. A printed message may comprise information as to which of the measured parameters caused the QC sample to fail the quality control. Together with a printout of the failing parameter a message suggesting which part of the oximeter needs repair or service, may be included. For example, the printed message may recommend a repair of the measurement section 76 of the spectrometer 1, if the measured wavelength shift $\Delta\lambda$ is larger than a predetermined threshold value stored in the memory of the oximeter.

In a preferred embodiment of the invention the measured parameters of the QC sample are used to modify spectra of standard blood samples corresponding to either of the QC levels 1–4.

Figure 8:
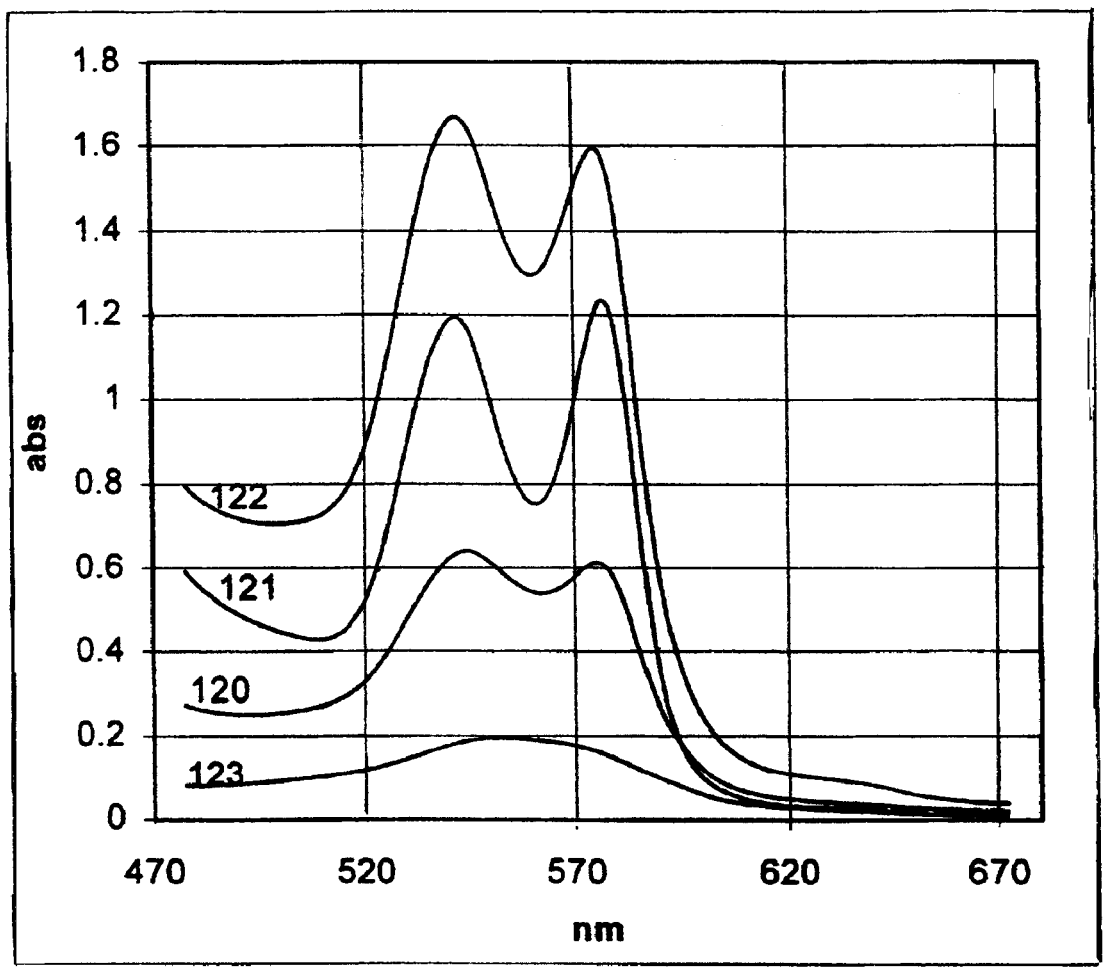
FIG. 8 shows absorption spectra of four standard blood samples related to quality control levels 1–4.

In FIG. 7 the figures in columns 2–7 of each row define a standard blood sample composition, and column 1 shows the related QC level. For each of the four standard blood samples a corresponding standard blood spectrum as shown in FIG. 8 may be derived mathematically by the processor in the oximeter from predetermined spectra of each blood component comprised in the standard blood samples. The predetermined spectra of each blood component are, preferably, stored in the memory of the oximeter during manufacturer.

Each blood component parameter value in the table in FIG. 7 has an attached plus/minus limit value. The limit values are calculated errors, which would be produced by a measurement of parameter values in the standard blood sample with an oximeter having a wavelength shift of plus and minus 0.05 nm, respectively, as the only measurement error. For example, the value of blood component FCOHb in a level 1 sample would be measured to 5.34% or 6.66% instead of the correct value of 6.00%. Thus, even very small wavelength shifts in the oximeter, introduces significant errors in the measured blood parameter values, thereby illustrating the importance of quality controlling the oximeter for wavelength shifts.

By determining the modifications to the mathematically derived standard blood spectrum related to the level of the actual QC sample under test resulting from the parameters $\Delta\lambda$, $c_{est}$ and optionally also $Q_{est}$, determined in the QC procedure, the oximeter may use the modified spectrum to calculate corresponding blood parameter values. The parameter values are reported to the operator of the oximeter, and the operator may compare them with assigned control limits for the actual QC level. The effect of the instrument errors revealed in the QC procedure on values reported for a blood sample with unknown blood parameter values may, e.g., appear from the deviations between the reported parameter values and the values of the relevant standard blood sample of FIG. 7.

FIG. 8 shows absorption spectra for each of standard blood sample, which absorption spectra are used in the oximeter for quality control levels 1–4. The spectra corresponding to levels 1–4 are 120, 121, 122, 123, respectively. Each spectrum has a corresponding $C_{ref}$ value corresponding to a Sulforhodamine B concentration.

The above modification to the standard blood spectra shown in FIG. 8 resulting from the parameter $\Delta\lambda$ is a shift along the wavelength axis corresponding to the difference between $\Delta\lambda$ and $\Delta\lambda_{qc}$ being either an assigned value or a predetermined fixed value stored in the memory of the oximeter. The modification of the standard blood spectra resulting from the parameter $c_{est}$ is a modification of the individual absorbances with the ratio $c_{est}/c_{ref}$.

By adopting this method of converting determined measurement errors introduced by the oximeter into parameter values of blood samples, instrument errors are reported in terms which are easily understood by the operator of the oximeter.

By noting which of the blood parameters failed the control, it may be possible to determine which of the measured parameters $\Delta\lambda$, $c_{est}$ and $Q_{est}$ caused the quality control to fail, and thereby determine which part of the oximeter that needs repair or service.

The relation between blood parameters that failed the quality control by being outside their corresponding control limits and the measured values of parameters $\Delta\lambda$, $c_{est}$, and $Q_{est}$ and thereby an error diagnosis of the oximeter may, preferably, be comprised in a service manual for a repair technician.

According to a preferred embodiment of the invention a method is provided for representing absorption spectra of one or several interfering components or substances contained in a blood sample in the oximeter. Preferably, the oximeter is adapted to repress the spectrum of Fetal Hemoglobin, which is known to cause significant interference in oximetry measurements.

In a predetermined blood sample spectrum, the absorbance $A_m(\lambda)$ recorded at each wavelength $\lambda$ contains contributions from each component in the sample. Interfering components are naturally treated as the other components. The magnitude of the contribution and thereby the concentration of each component in the sample is determined according to equation (18)

$$c_y = K_y(\lambda) \cdot A_m(\lambda).$$

The vector $K_y(\lambda)$ are predetermined and stored in the memory of the spectrophotometer.

By including a Fetal Hemoglobin component in a blood sample, of which the reference spectrum is to be determined, a vector $K_{fetal}(\lambda)$ corresponding to the concentration of Fetal Hemoglobin in the sample, is determined.

Preferably, the oximeter further provides a predetermined vector $A_{fetal}(\lambda)$, representing the difference spectrum between Adult Hemoglobin and Fetal Hemoglobin. The vector $A_{fetal}(\lambda)$ is, preferably, determined at a reference concentration $c_{fetal}$ of 1 mmol/L.

The effect on determined blood parameter values due to the presence of Fetal Hemoglobin in the blood sample, is minimised by repressing the spectrum of Fetal Hemoglobin.

The first stage in the repression process comprises the determination of the concentration of Fetal Hemoglobin in the blood sample, according to equation (19)

$$c_{fetal} = K_{fetal}(\lambda) \cdot A_m(\lambda).$$

The second stage comprises the determination of a modified spectrum by subtracting the difference spectrum at the determined concentration from the measured spectrum $A_m(\lambda)$ of the blood sample, if $c_{fetal}$ is greater than a predetermined threshold value, according to equation (20)

$$A_{mod}(\lambda) = A_m(\lambda) - \frac{c_{fetal}}{1} A_{fetal}(\lambda)$$

wherein $A_{mod}(\lambda)$ is the modified spectrum and $c_{ref} = 1$ mmol/L.

If $c_{fetal}$ is smaller than the predetermined threshold value the modified spectrum is set equal to the measured spectrum $A_m(\lambda)$.

The third stage comprises the determination of concentrations of blood components $c_y$ from the modified spectrum $A_{mod}(\lambda)$, whereby the effect of Fetal Hemoglobin in the blood sample or determined concentrations $c_y$ of blood components is minimised.

By representing the spectrum of Fetal Hemoglobin automatically, an oximeter is provided with an increased precision in measured blood parameter values, and an easier operation than currently available instruments.

Figure 9:
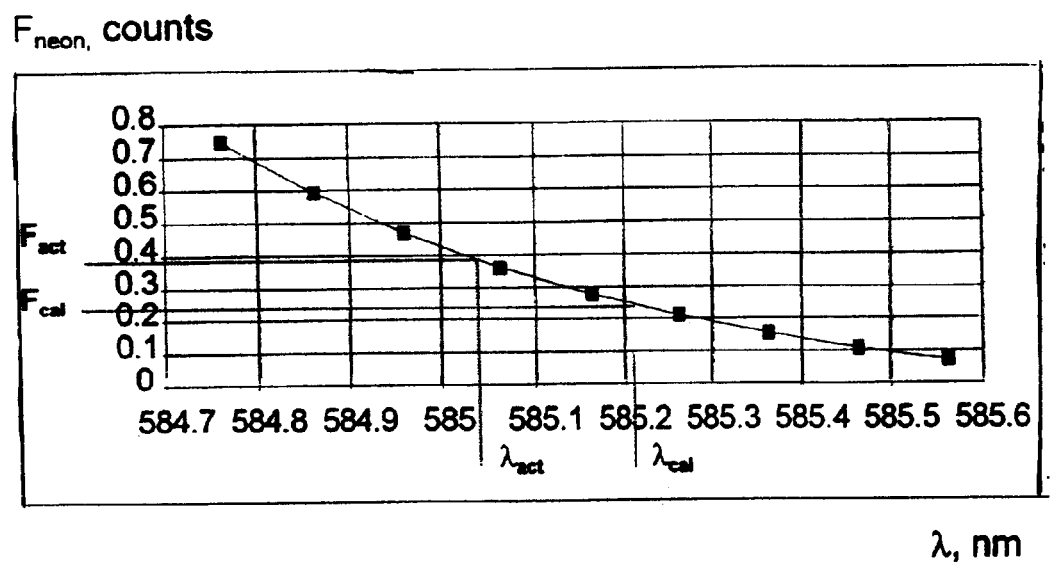
FIG. 9 is a graph of a variable $F_{neon}$ plotted against the wavelength of light striking two photodiodes in the spectrometer.

According to a preferred embodiment of the invention, FIG. 9 is a graph of a variable $F_{neon}$ plotted against the wavelength of light striking two photodiodes in wavelength channels 70 and 71 of the photodiode array 83 in the spectrometer 1 shown in FIG. 3. The spectrometer 1 comprises a neon glow lamp (not shown), which emits at least one spectral line at a highly accurate reference wavelength of 585.25 nm, suitably positioned within the preferred wavelength range from 480 to 670 nm. The accurate wavelength of the emitted spectral line is used in the oximeter as a reference wavelength against which the location of the 128 wavelength channels of the array 83 is adjusted. To utilise the reference wavelength a variable $F_{neon}$ is defined as $$F_{neon} = R(70)/R(71) \tag{32}$$

wherein R(70) and R(71) are the magnitudes of the current or the response in each of the photodiodes located in channels 70 and 71. $F_{neon}$ is also equal to the ratio between the light intensity striking photodiodes in channels 70 and 71, due to the linear relationship between the current in a photodiode and the light intensity which strikes it. For example, if $F_{neon} = 1$ the light intensity striking diode 70 is equal to the light intensity striking diode 71, which means that the reference wavelength is positioned exactly between the channels 70 and 71. $F_{neon}$ is used as a variable that defines the position of the light of the reference wavelength emitted from the neon lamp relative to the wavelength channels in the spectrometer 1. This characteristic of $F_{neon}$ is utilised during field operation of the oximeter, where the value of $F_{neon}$ is measured at predetermined time intervals, and compared with a reference value $F_{cs1}$ stored in the memory of the oximeter during manufacture.

The spectrometer 1 is scanned with light emitted from a high precision monochromator in the wavelength range 585.25+/−7.5 nm during manufacture. A response curve for the photodiode located in channel 71 is measured. An example of a measured response curve is 131 shown in FIG. 10. A calibration algorithm comprised in the memory of the oximeter calculates a corresponding response curve for channel 70 by shifting the wavelength axis. The calibration algorithm further calculates a wavelength calibration table comprising values of the variable $F_{neon}$ and the corresponding value of the wavelength of light emitted from the monochromator by using the determined response curves of channels 70 and 71. The oximeter stores determined values of the wavelength calibration table in the memory. A reference value of $F_{neon}$, denoted $F_{cal}$, is determined during manufacture by activating the neon lamp and measuring the response of channels 70 and 71, as previously described. The reference value of $F_{cal}$ is stored in the memory of the oximeter.

The data comprised in the wavelength calibration table may be displayed graphically as shown in FIG. 9.

A calibration program measures the current temperature of the spectrometer 1 between two blood sample measurements in the normal operation of the oximeter. The cuvette is always cleaned with a transparent rinse solution between two blood sample measurements. The current measured temperature of the spectrometer 1 is compared with a previous temperature measurement which was performed at the time of the previous neon lamp activation and stored in the memory of the oximeter. The calibration program determines whether the current temperature value deviates more than 0.3° C. from the previous temperature value, and performs a measurement of the current value of $F_{neon}$ if this is the case.

The graph in FIG. 9 is now used to illustrate how a wavelength shift of the oximeter is determined and compensated during a period of time between two blood sample measurements, wherein the cuvette is rinsed. A first value of $F_{neon}$ denoted $F_{cal}$ corresponding to a first value of the wavelength denoted $\lambda_{cal}$ are shown in the graph, and the value of $F_{cal}$ is determined, as previously described. A second value of the variable $F_{neon}$ denoted $F_{act}$ may be measured by the oximeter between two blood sample measurements. By utilising the predetermined wavelength calibration table comprised in the memory of the oximeter a second value of wavelength λ denoted $\lambda_{act}$ corresponding to $F_{act}$ may be determined. The value of $\lambda_{act}$ may be determined from the discrete values of the variable λ comprised in the calibration table according to well-known mathematical interpolation methods such as linear interpolation, polynomial interpolation, cubic spline interpolation, etc.

A wavelength shift Δλ of the spectrometer may be determined from the difference between the determined value $\lambda_{act}$ and the calibration value $\lambda_{cal}$. The determined wavelength shift Δλ of the spectrometer 1 may be utilised to compensate a measured absorption spectrum $A_m(\lambda)$ of a fluid sample by determining a modified absorption spectrum $A_{modi}(\lambda)$ of the sample, wherein the effect of the determined wavelength shift Δλ on absorbances in the measured spectrum $A_a(\lambda)$ is removed.

The modified spectrum is, preferably, determined by first utilising a cubic spline function to generate interpolated absorbance values between the discrete values at the 128 wavelengths in the measured spectrum $A_m(\lambda)$. The modified spectrum $A_{modi}(\lambda)$ is determined by shifting the wavelength of each measured absorbance value in $A_m(\lambda)$ sequentially with an amount equal to Δλ and determine a corresponding interpolated absorbance value for the modified spectrum.

The provision of a spectral lamp, preferably a neon lamp, having at least one spectral line within a desired wavelength range enables the oximeter to perform highly accurate measurements of the wavelengths of light absorbed by a sample by comparing the determined wavelength of said at least one spectral line with the assigned wavelength of the spectral line stored in the memory of the oximeter, calculating the possible wavelength shift, and compensating the determined absorbance of the sample for said wavelength shift. Accordingly, the determined absorption spectrum by the spectrometer 1 is being compensated for wavelength shifts resulting from manufacturing tolerances and temperature drift during the use of the oximeter, thereby providing accurate measurements of blood parameter values.

Figure 10:
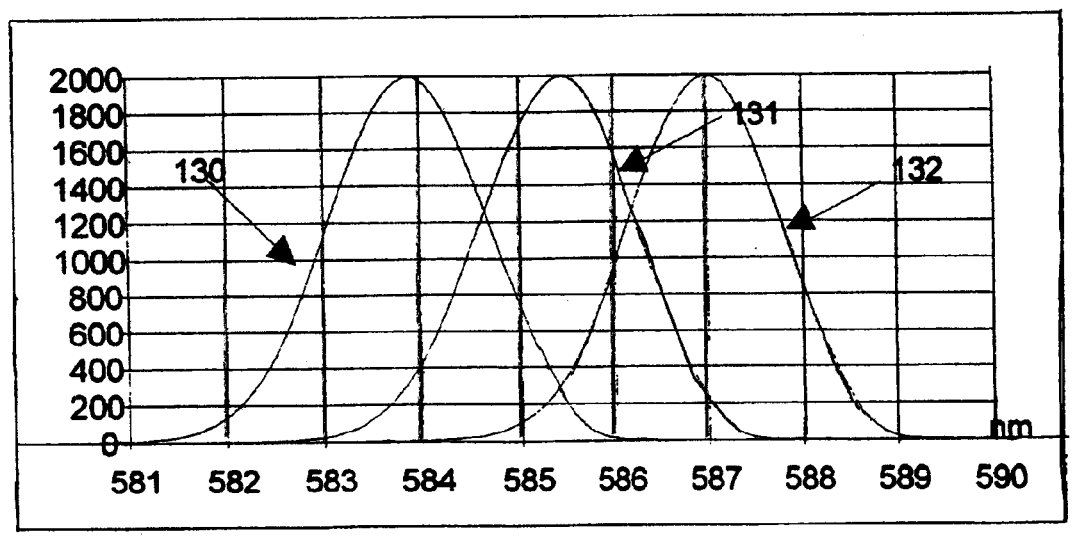
FIG. 10 shows response curves of photodiodes located in wavelength channels 70, 71 and 72.

FIG. 10 shows three response curves 130, 131 and 132 of photodiodes located in the corresponding wavelength channels 70, 71 and 72. The x-axis of the graph is the wavelength in nm of the light striking the diodes, and the y-axis of the graph is counts. The wavelength distance between the peak points of e.g. response curve 130, 131 is approximately 1.5 nm, which is the channel distance between all the 128 adjacent wavelength channels of the diode array 13.

What is claimed is:

1. A quality control method for a spectrophotometer, comprising the steps of:
    determining with the spectrophotometer an absorption spectrum $A_m(\lambda)$ of a fluid quality control sample containing a dye selected from such dyes which provide the quality control sample with an absorption spectrum with a significant absorbance peak showing a steep flank,
    determining a wavelength shift Δλ between the absorption $A_m(\lambda)$ of the actually measured quality control sample and a reference absorption spectrum $A_0(\lambda)$ of a reference quality control sample containing the dye stored in a memory of the spectrophotometer, and
    comparing Δλ with $\Delta\lambda_{qc}$, wherein $\Delta\lambda_{qc}$ is a wavelength shift assigned to the quality control sample.

2. A method according to claim 1, wherein the wavelength shift Δλ is determined from $A_m(\lambda)$ and a predetermined mathematical parameter stored in the memory of the spectrophotometer.

3. A method according to claim 2, wherein the mathematical parameter is a coefficient vector $C_{\Delta\lambda}(\lambda)$ and wherein the wavelength shift Δλ is determined from $C_{\Delta\lambda}(\lambda) \cdot A_m(\lambda)$.

4. A method according to claim 3, wherein the vector $C_{\Delta\lambda}(\lambda)$ fulfills the equation $$\Delta\lambda = C_{\Delta\lambda}(\lambda) \cdot A_m(\lambda).$$

5. A method according to claim 4, wherein $C_{\Delta\lambda}(\lambda)$ has been determined from a Taylor series of the reference absorption spectrum $A_0(\lambda)$.

6. A method according to claim 5, wherein $C_{\Delta\lambda}(\lambda)$ has been determined from a combination of the reference absorption spectrum $A_0(\lambda)$ and a first derivative $A_0'(\lambda)$ of said reference absorption spectrum.

7. A method according to claim 1, wherein the wavelength shift Δλ is determined after normalisation of the determined spectrum $A_m(\lambda)$ with an estimate of the concentration of the dye.

8. A method according to claim 1, wherein the quality control sample has a known dye concentration $C_{qc}$ and the dye comprises a first and a second component, the method further comprising the steps of
    calculating parameters $s_1$ and $s_2$ from
    $s_1 = C_1(\lambda) \cdot A_m(\lambda)$
    $s_2 = C_2(\lambda) \cdot A_m(\lambda)$
    in which $C_1(\lambda)$ and $C_2(\lambda)$ are predetermined vectors previously stored in the memory of the spectrophotometer, and
    calculating an estimated concentration $C_{est}$ of the dye from
    $C_{est} = a\, s_1 + b\, s_2$
    in which a and b are predetermined constants previously stored in the memory of the spectrophotometer.

9. A method according to claim 8, further comprising the step of comparing $C_{est}$ and $C_{qc}$.

10. A method according to claim 8, further comprising the step of calculating a variable $Q_{est} = s_{2est}/s_{1est}$.

11. A method according to claim 10, wherein the quality control sample has an assigned value of $Q_{qc} = s_{2qc}/s_{1qc}$, which method further comprises the step of comparing $Q_{est}$ with $Q_{qc}$.

12. A method according to claim 1, wherein the spectrophotometer is an oximeter.

13. A method according to claim 12, wherein spectra are measured in the wavelength range from 400 to 800 nm.

14. A method according to claim 12, further comprising the step of determining estimated errors in blood parameter values reported by the oximeter caused by the wavelength shift Δλ.

15. A method according to claim 8, wherein the spectrophotometer is an oximeter, further comprising the step of determining estimated errors in blood parameter values reported by the oximeter caused by a difference between $C_{est}$ and $C_{qc}$.

16. A method according to claim 11, wherein the spectrophotometer is an oximeter, further comprising the step of determining estimated errors in blood parameter values reported by the oximeter caused by a difference between $Q_{est}$ and $Q_{qc}$.

17. A method according to claim 1 further comprising the steps of:
    determining a first reference absorption spectrum $A_{01}(\lambda)$ of a reference sample containing a dye in a first concentration with a reference spectrophotometer,
    determining a first derivative $A_{01}'(\lambda)$ of the first reference spectrum, and determining from at least the first reference spectrum $A_{o1}(\lambda)$ and the first derivative $A_{o1}'(\lambda)$ a mathematical parameter from which a wavelength shift $\Delta\lambda$ of the spectrophotometer can be determined, and storing the mathematical parameter in a memory of the spectrophotometer.

18. A method according to claim 17, wherein the step of determining the mathematical parameter comprises the steps of calculating a set of calibration vectors $B_i(\lambda)$ according to
$B_i(\lambda)=s_i A_1(\lambda)+s_{i3} A_{o1}'(\lambda)$
in which i=1, 2, ..., N (N>1) and $s_i$ and $s_{i3}$ are constants of selected values, determining a coefficient vector $C_{\Delta\lambda}(\lambda)$ constituting the mathematical parameter so that each set of corresponding values $s_{i3}$, $B_i(\lambda)$ satisfies:

$s_{i3}=C_{\Delta\lambda}(\lambda)\cdot B_i(\lambda)$, i=1,2, ..., N.

19. A method according to claim 17, wherein the dye comprises a first component and a second component, and further comprising the step of determining a second reference $A_{o2}(\lambda)$ of a second reference sample containing the dye in a second concentration with the reference spectrophotometer, and wherein the step of determining a mathematical parameter comprises the steps of calculating a set of vectors $B_i(\lambda)$ from
$B_i(\lambda)=s_{i1} A_1(\lambda)+s_{i2} A_2(\lambda)+S_{i3} A_o'(\lambda)$
in which $A_1(\lambda)$ and $A_2(\lambda)$ are derived from the first and second reference spectra $A_{o1}(\lambda)$, $A_{o2}(\lambda)$ and represent spectral information about the first and second components, respectively, and i=1, 2, ..., N (N>1), and $S_{i1}$, $S_{i2}$ and $S_{i3}$ are constants of selected values, determining a vector $C_{\Delta\lambda}(\lambda)$ constituting the mathematical parameter so that $s_{i3}C_{\Delta\lambda}(\lambda)\cdot B_i(\lambda)$.

20. A spectrophotometer comprising a processor that is adapted to determine the wavelength shift $\Delta\lambda$ between an absorption spectrum $A_m(\lambda)$ determined with the spectrophotometer on a fluid quality control sample containing a dye selected from such dyes which provide the quality control sample with an absorption spectrum with a significant absorbance peak showing a steep flank and a reference absorption spectrum $A_0(\lambda)$ of a reference quality control sample containing the dye, stored in a memory of the spectrophotometer wherein the quality control sample has an assigned wavelength shift $\Delta\lambda_{qc}$, and wherein the processor is adapted to compare $\Delta\lambda$ with $\Delta\lambda_{qc}$.

21. A spectrophotometer according to claim 20, wherein the wavelength shift $\Delta\lambda$ is determined from $A_m(\lambda)$ and a predetermined mathematical parameter stored in the memory of the spectrophotometer.

22. A spectrophotometer according to claim 21, wherein the mathematical parameter is a coefficient vector $c_{\Delta2}(\lambda)$ and wherein the wavelength shift $\Delta$ is determined from $C_{\Delta\lambda}(\lambda)\cdot A_m(\lambda)$.

23. A spectrophotometer according to claim 22, wherein the vector $C_{\Delta\lambda}(\lambda)$ fulfills the equation $\Delta\lambda=C_{\Delta\lambda}(\lambda)\cdot A_m(\lambda)$.

24. A spectrophotometer according to claim 23, wherein $C_{\Delta\lambda}(\lambda)$ has been determined from a Taylor series of the reference absorption spectrum $A_0(\lambda)$.

25. A spectrophotometer according to claim 24, wherein $C_{\Delta\lambda}(\lambda)$ has been determined from a combination of the reference absorption spectrum $A_0(\lambda)$ and a first derivative $A_0'(\lambda)$ of said reference absorption spectrum.

26. A spectrophotometer according to claim 20, wherein the wavelength shift $\Delta\lambda$ is determined after normalisation of the determined spectrum $A_m(\lambda)$ with an estimate of the concentration of the dye.

27. A spectrophotometer according to claim 20, wherein the quality control sample has a known dye concentration $C_{qc}$ and the dye comprises a first and a second component, and wherein the processor is adapted to calculate parameters $s_1$ and $s_2$ from $s_1=C_1(\lambda)\cdot A_m(\lambda)$ $s_2=C_2(\lambda)\cdot A_m(\lambda)$ in which $C_1(\lambda)$ and $C_2(\lambda)$ are predetermined vectors previously stored in the memory of the spectrophotometer, and calculate an estimated concentration $C_{est}$ of the dye from $C_{est}=a\ s_1+b\ s_2$ in which a and b are predetermined constants previously stored in the memory of the spectrophotometer.

28. A spectrophotometer according to claim 27, wherein the processor is further adapted to compare $C_{est}$ with $C_{qc}$.

29. A spectrophotometer according to claim 27, wherein the processor is further adapted to calculate a variable $Q_{est}=s_{2est}/s_{1est}$.

30. A spectrophotometer according to claim 29, wherein the quality control sample has an assigned value of $Q_{qc}=s_{2qc}/s_{1qc}$ and wherein the processor is further adapted to compare $Q_{est}$ and $Q_{qc}$.

31. A spectrophotometer according to claim 20 which is an oximeter.

32. A spectrophotometer according to claim 31, wherein spectra are measured in the wavelength range from 400 to 800 nm.

33. A spectrophotometer according to claim 31, wherein the processor is adapted to determine estimated errors in blood parameter values reported by the spectrophotometer caused by the wavelength shift $\Delta\lambda$.

34. A spectrophotometer according to claim 27, wherein the spectrophotometer is an oximeter and the processor is further adapted to determine estimated errors in blood parameter values reported by the spectrophotometer caused by a difference between $C_{est}$ and $C_{qc}$.

35. A spectrophotometer according to claim 30, wherein the spectrophotometer is an oximeter and the processor is further adapted to determine estimated errors in blood parameter values reported by the spectrophotometer caused by a difference between $Q_{est}$ and $Q_{qc}$.

36. A spectrophotometer according to claim 20 for the determination of a concentration $c_y$ of a component y of a sample and wherein the memory further comprises at least one vector $A_{int}(\lambda)$ representing spectral information of an interfering component in the sample at a concentration $C_{ref}$, and at least one predetermined vector $K_{int}(\lambda)$ and wherein the processor is further adapted to calculate the concentration $C_{int}$ of the interfering component according to $C_{int}=K_{int}(\lambda)\cdot A_m(\lambda)$, and if $C_{int}$ is greater than a predetermined threshold value, $C_{ref}$, calculate a modified absorbance spectrum $A_{mod}(\lambda)$ according to $$A_{mod}(\lambda) = A_m(\lambda) - \frac{C_{int}}{C_{ref}} A_{int}(\lambda), \text{ and}$$

determine $c_y$ from the modified spectrum $A_{mod}(\lambda)$ according to $$C_y = K_y(\lambda) \cdot A_{mod}(\lambda)$$

where $K_y(\lambda)$ is a predetermined vector and whereby the effect of interfering components on determined concentrations $C_y$ is minimised.

37. A spectrophotometer according to claim 36, wherein the interfering component is fetal hemoglobin.

* * * * *